United States Patent [19]

Backlund

[11] 4,419,184

[45] Dec. 6, 1983

[54] METHOD FOR CONTROL OF CHEMICALS DURING GAS TREATMENT OF SUSPENSIONS

[75] Inventor: Ake Backlund, Karlstad, Sweden

[73] Assignee: Kamyr AB, Karlstad, Sweden

[21] Appl. No.: 284,815

[22] Filed: Jul. 20, 1981

[30] Foreign Application Priority Data

Aug. 26, 1980 [SE] Sweden .............................. 8005959

[51] Int. Cl.$^3$ ................................................ D21C 7/12
[52] U.S. Cl. ....................................... 162/49; 162/62; 162/65; 422/111
[58] Field of Search ..................... 162/49, 62, 238, 65; 422/62, 111; 23/230 A

[56] References Cited

U.S. PATENT DOCUMENTS

| | | | |
|---|---|---|---|
| 3,745,065 | 7/1973 | Nilo Rama ............................ | 162/49 |
| 3,832,276 | 8/1974 | Roymoulik et al. ................. | 162/65 |
| 3,951,733 | 4/1976 | Phillips ................................ | 162/65 |
| 4,093,511 | 6/1978 | Richter ................................ | 162/65 |
| 4,220,498 | 9/1980 | Prough ................................ | 162/65 |
| 4,239,590 | 12/1980 | Prough ................................ | 162/49 |
| 4,259,150 | 3/1981 | Prough ................................ | 162/65 |

FOREIGN PATENT DOCUMENTS

| | | | |
|---|---|---|---|
| 2819860 | 11/1978 | Fed. Rep. of Germany ........ | 162/49 |
| 702087 | 12/1979 | U.S.S.R. ............................. | 162/238 |

OTHER PUBLICATIONS

Oxygen/Alkali Delignification at Kamyr Digester Blowline Consistency—A Status Report by: P. J. Kleppe, A. Backlund, and Y. Schildt (vol. 59, No. 11, Nov. 1976).

Burnett, "Computer Control of the Chlorine Stage" Pulp and Paper Magazine of Canada, vol. 71, No. 14, Jul. 17, 1970.

McGill, "Measurement and Control in Papermaking", Adam Hilger Ltd., Bristol 1980.

*Primary Examiner*—Steve Alvo
*Attorney, Agent, or Firm*—Cushman, Darby & Cushman

[57] ABSTRACT

A method of treating medium consistency paper pulp or the like with a treament gas, such as oxygen, is provided to achieve uniform treatment results. The treatment gas is added to the pulp in finely distributed small bubbles, and the density of the suspension is measured at at least one moment, or the average density is measured during at least one time period. The temperature and the pressure of the suspension corresponding to the density measurements are determined, and the rest gas content of the substance is calculated at the actual moments or time periods based upon the measurements in the preceding steps. The gas consumption is then calculated as the difference between the quantity of gas added, and the residual gas quantity, or between two residual gas quantities. The gas addition step is controlled based upon the calculated consumption to obtain substantially uniform treatment results.

15 Claims, No Drawings

METHOD FOR CONTROL OF CHEMICALS DURING GAS TREATMENT OF SUSPENSIONS

BACKGROUND AND SUMMARY OF THE INVENTION

The invention relates to the treatment of a substance with a treatment gas. The substance may be a liquid or may be in suspended form in a liquid, and in the following specification and claims the term "suspension" is intended to encompass both these forms of the substance. The invention is particularly applicable to a suspension of comminuted cellulosic fibrous material and utilizing an oxygen or oxygen containing gas for bleaching or delignification of the material.

Conventional commercial oxygen bleaching of paper pulp, utilizing apparatus such as disclosed in U.S. Pat. No. 3,660,225, normally takes place with the consistency of the pulp in the range of 20 to 30%. The degree of delignification (quantified by the KAPPA number of the pulp) is controlled mainly by varying the amount of sodium hydroxide (NaOH). The KAPPA number of the unbleached pulp is determined, and the addition of NaOH is varied with about 1 kilogram of NaOH per ton of air-dried pulp (ADMT) for each desired integer change of the KAPPA number. The temperature and the partial pressure of the oxygen is normally kept constant. During such high pulp concentration bleaching with oxygen an adequate quantity of oxygen is at all times maintained available as long as the pressure in the treatment vessel and the oxygen quantity in the reactor gas are kept about constant.

During conventional continuous oxygen bleaching of medium consistency pulp (e.g. in the range of 5 to 15% consistency) the available oxygen at all times is determined by the quantity of oxygen which is continuously added per ton of pulp. If the oxygen consumption increases due to higher washing loads in the preceding treatment stage, or due to a higher KAPPA number of the pulp, a lack of oxygen may appear at the end of the reaction cycle, which results in insufficient delignification (i.e., a KAPPA number that is too high) of the treated pulp. In order to maintain an effective control of the KAPPA number it is therefore important that the oxygen addition can be adjusted automatically during the treatment process, primarily to compensate for variations in washing losses and in the unbleached KAPPA number of the pulp.

According to the present invention a method is provided which provides for effective control of the oxygen addition so that a uniform delignification of the pulp occurs. While the invention is described primarily with respect to pulp treatment, it is to be understood that it is also applicable to other systems for the gas treatment of a suspension, and results in uniform treatment of the suspension in each case. The invention is based upon the observation that the pressure in a closed vessel filled with pulp in which oxygen is mixed-in decreases as the oxygen is consumed. Utilizing this observation, the gas consumption can be determined by measuring the density of the pulp at various stages, calculating the residual gas content of the pulp, calculating the gas consumption, and controlling the addition of gas based upon the gas consumption calculations.

DETAILED DESCRIPTION OF THE INVENTION

The physical observation upon which the invention is based is that the pressure in a closed vessel filled with oxygen-mixed pulp decreases as the oxygen is consumed. Utilizing this observation it is possible to provide a simple method for measuring the oxygen consumption in a continuously operating, bleaching or delignification stage on a commercial scale. Experimentally it has been shown that of an original quantity of oxygen, well-mixed into the pulp, corresponding to 28 kilograms per ton absolutely dry pulp (kg/BDMT), the following quantities remained after the passage of zero to forty minutes in a closed vessel, while the pressure decreased as indicated:

TABLE I

| Time, min. | % $O_2$ Remaining | $O_2$ [kg/BDMT] | Pressure kp/cm$^2$ |
|---|---|---|---|
| 0 | 100.0 | 28.0 | 5.8 |
| 1 | 70.7 | 19.8 | 4.4 |
| 2 | 56.4 | 15.8 | 3.5 |
| 3 | 46.8 | 13.1 | 3.1 |
| 4 | 40.7 | 11.4 | 2.9 |
| 5 | 35.0 | 9.8 | 2.1 |
| 10 | 17.9 | 5.0 | 1.3 |
| 20 | 13.2 | 3.7 | 0.8 |
| 30 | 8.2 | 2.3 | 0.5 |
| 40 | 3.6 | 1.0 | 0.4 |

During oxygen bleaching of pulp in practical operation in the trade, medium consistency (e.g. 5 to 15%) pulp is integrally mixed with oxygen so that the gas is present as small bubbles. Typical apparatus for effecting such mixing is disclosed in U.S. Pat. No. 4,093,511 (the disclosure of which is hereby incorporated by reference herein). Other chemicals (e.g. NaOH) may also be mixed in at this time, and the pulp is fed in a continuous flow to a first end of a vertical treatment vessel. The pressure in the vertical treatment vessel is maintained substantially constant, and the temperature is normally maintained above 80° C., and preferably within the range of about 95° to 120° C. From the second end of the vessel the pulp is led to a flash cyclone, or to another subsequent treatment apparatus. Due to the fact that the pressure in the treatment vessel is kept substantially constant (and is superatmospheric), the consumption of gas in the pulp will correspond to a reduction of the volume of the bubbles, which in turn means that the pulp—with gas bubbles—increases in density during a reaction.

Based on the results from Table I showing the remaining oxygen pressure and by utilizing the universal gas law $pv=nRT$, density variations that will occur can be determined. For instance, assuming that the working pressure is 8 bars absolute and a temperature of about 105° C. (the steam pressure at 105° C. is 1.3 bars), and by applying the universal gas law wherein $p=6.7$ bars $(8-1.3)$, and $n=q \div 32$ ($q$=the quantity of oxygen gas in kilograms), it follows that $v=0.14\ q$ (in cubic meters). Also assuming a pulp consistency of 10%, wherein there is then 9.0 tons of liquid with a density of 0.95 and a volume of 9.47 cubic meters and 1.0 tons pulp with a density of 1.50 and a volume of 0.66 cubic meters (total volume 10.14 cubic meters), the following relationships are valid:

TABLE II

| Time (Min) | Gas Volume (m³) | Total volume (m³) | Density (tons/m³) |
|---|---|---|---|
| 0 | 3.92 | 14.06 | 0.71 |
| 1 | 2.77 | 12.91 | 0.77 |
| 2 | 2.21 | 12.35 | 0.81 |
| 3 | 1.83 | 11.97 | 0.84 |
| 4 | 1.60 | 11.73 | 0.85 |
| 5 | 1.37 | 11.51 | 0.87 |
| 10 | 0.70 | 10.84 | 0.92 |
| 20 | 0.52 | 10.65 | 0.94 |
| 30 | 0.32 | 10.46 | 0.96 |
| 40 | 0.14 | 10.28 | 0.97 |

Applying the above information in practical operation, the gas consumption can be determined by measuring the density of the pulp at a moment after the gas has been mixed into the pulp and distributed into small bubbles. Simultaneously, the pulp pressure and pulp temperature are measured after gas addition, and the gas consumption is apparent as the difference between added and calculated residual gas at the actual moment of measurement. On this basis, the gas addition to the pulp is then regulated taking into account the desired final treatment results (e.g. degree of delignification). Even better control may be provided if the density is measured and the residual gas content is calculated at several time intervals after the addition of the gas. Further, it is also possible to compare the consumption between two or more such time intervals and in such a way obtain a picture of the reaction process during the entire treatment cycle. Also, instead of making a measurement at a specific moment it may be advantageous to calculate the average density during one or more short time periods.

According to one aspect of the method according to the invention, gas treatment of a suspension (particularly medium consistency comminuted fibrous cellulosic material) is practiced by: (a) Adding a quantity of treatment gas to the substance in the form of finely distributed small bubbles. (b) Determining the density of the substance at at least one moment. (c) Measuring the temperature and the pressure of the substance corresponding to the density determination of step (b). (d) Calculating the residual gas content of the suspension at the at least one moment based upon the information determined according to steps (b) and (c). (e) Calculating the gas consumption as a difference between the gas quantity added according to step (a), and the residual gas quantity claculated accordingly to step (d); and (f) controlling the quantity of gas added in step (a) based upon the consumption according to step (e) to obtain uniform treatment of the suspension, or any other desired treatment results.

According to another aspect of the invention, another method may be practiced substantially the same as the method described above except for differences in the practice of steps (b) and (e). In this aspect of the method according to the invention, according to step (b) the average density of the suspension is measured during at least one time period. In the practice of step (e), then, the gas consumption is calculated as the difference between two residual gas quantities calculated according to step (d).

In the practice of step (b) according to the present invention, a variety of different procedures and apparatus may be utilized. One preferred procedure is to determine the density by measuring the difference is static pressure between different measuring points. Since treatment is preferably accomplished in a vertical treatment vessel, the pressure difference may be determined by means of dp cells between different heights in the vessel. If the pulp did not contain any gas, the density of the pulp should be the normal density for the pulp at that particular level. However, if the pulp does contain gas of a certain volume at a certain height in the reaction vessel, the density will be different at the same time as the pressure difference between various levels will be changing, as long as gas is consumed and the volume is decreasing.

Another manner of determining density in practicing method step (b) according to the invention is by utilizing a density measuring device utilizing radioactivity. One such device is a gamma radiation absorption device such as shown in U.S. Pat. No. 4,239,590 (the disclosure of which is hereby incorporated by reference herein).

A third alternative procedure utilizable in the practice of method step (b), applicable where the average density of the suspension is measured during at least one time period, is to continuously weigh the reaction vessel and its contents. Utilizing such a procedure it is possible to obtain a measurement of the average content of gas in the pulp and how this changes with varying changes of gas addition.

The method steps (a) through (f) are preferably practiced continuously, with the suspension moving in a substantially constant volume flow, and with the gas being added and mixed into the suspension is a substantially even flow. The suspension is transported to a substantially vertical treatment vessel which is maintained at substantially constant superatmospheric pressure and at a temperature above 80° C. The suspension, in the case of paper pulp, is preferably passed into the treatment vessel without pumping by utilizing the higher pressure in a preceding treatment stage, preferably the pressure in a continuous digestor. The pulp is passed to the first end of the treatment vessel, with the gas addition taking place just prior to passage into the treatment vessel, and the treated pulp (with any remaining residual gas) is continuously removed from the vessel second end. The density values determined are adjusted to take into account possible variations in the flow velocity of the suspension through the vessel, which flow velocity also may be sensed utilizing conventional apparatus (again see U.S. Pat. No. 4,239,590), and appropriately introduced into the calculations.

It will thus be seen that according to the present invention a method is provided which provides for the control of treatment gas added to a suspension in such a way that the suspension achieves a desired degree of treatment. The invention is particularly useful in obtaining a uniform delignification of comminuted cellulosic fibrous material suspensions of medium (e.g. 5 to 15%) consistency.

While the invention has been herein shown and described in what is presently conceived to the most practical and preferred embodiment thereof, it will be apparent to those of ordinary skill in the art that many modifications may be made thereof within the scope of the invention, which scope is to be accorded the broadest interpretation of the appended claims so as to encompass all equivalent methods or procedures.

What is claimed is:

1. A method of treating a pulp suspension with a treatment gas comprising the steps of:

(a) adding a quantity of treatment gas to the pulp suspension in the form of finely distributed small bubbles the gas selected from the group consisting essentially of oxygen and oxygen containing gas;
(b) after step (a), determining the density of the suspension containing the treatment gas at at least one moment;
(c) simultaneously measuring the temperature and pressure of the suspension containing the treatment gas corresponding to the density determined during step (b);
(d) calculating the residual gas content of the suspension at the at least one moment at which the density is determined, the calculation utilizing the information determined in steps (b) and (c);
(e) calculating the gas consumption as the difference between the quantity of gas added in step (a) and the residual gas quantity calculated according to step (d);
(f) controlling the quantity of gas added in step (a) based upon the consumption calculation in step (e) to obtain a desired resultant treatment of the suspension; and
wherein steps (b) through (f) are practiced while maintaining the suspension at a substantially contant superatmospheric pressure.

2. A method as recited in claim 1 wherein step (b) is practiced so that the density of the suspension is determined at a plurality of moments.

3. A method as recited in claim 2 wherein steps (a) through (f) are practiced continuously with the suspension moving in a substantially constant volume flow, and with the treatment gas being added and mixed into the suspension in a substantially even flow.

4. A method as recited in claim 3 wherein the suspension is passed through a substantially vertical treatment vessel maintained at substantially constant superatmospheric pressure and at a temperature above 80° C.; and wherein step (b) is practiced by measuring the static pressure difference between two or more levels in the vertical treatment vessel.

5. A method as recited in claim 3 wherein the suspension moves through a substantially vertical treatment vessel maintained at substantially constant superatmospheric pressure and at a temperature above 80° C.; and wherein step (b) is accomplished by utilizing a device utilizing radioactivity.

6. A method of treating a pulp suspension with a treatment gas comprising the steps of:
(a) adding a quantity of treatment gas to the pulp suspension in the form of finely distributed small bubbles the gas selected from the group consisting essentially of oxygen and oxygen containing gas;
(b) after step (a), determining the average density of the suspension containing the treatment gas during at least one time period;
(c) simultaneously measuring the temperature and pressure of the suspension containing the treatment gas corresponding to the density measurement according to step (b);
(d) calculating the residual gas content of the suspension during the time period during which the average density is determined, utilizing the information determined according to steps (b) and (c);
(e) calculating the gas consumption as the difference between two residual gas quantities calculating according to step (d);
(f) controlling the quantity of gas added in step (a) based upon the consumption calculated according to step (e) to obtain a desired resultant treatment of the suspension; and
wherein steps (b) through (f) are practiced while maintaining the suspension at a substantially contant superatmospheric pressure.

7. A method as recited in claims 1 or 6 wherein steps (b) through (f) are practiced at a temperature above 80° C.

8. A method as recited in claim 2 or 3 wherein the suspension comprises a suspension of comminuted cellulosic fibrous material having a consistency of about 5 to 15%.

9. A method as recited in claim 8 wherein steps (a) through (f) are performed continuously with the suspension moving in a substantially constant volume flow and with the treatment gas added and mixed into the suspension in a substantially even flow.

10. A method as recited in claim 8 wherein steps (a) through (f) are performed continuously with the suspension moving in a substantially constant volume flow, and wherein the treatment gas is added and mixed into the suspension in a substantially even flow; and wherein the suspension moves through a substantially vertical vessel maintained a substantially constant superatmospheric pressure, and at a temperature above 80° C.; and wherein step (b) is practiced so that the density values obtained are adjusted to take into account possible variations in the flow velocity of the suspension through the vessel.

11. A method as recited in claim 8 wherein steps (a) through (f) are practiced continuously with the suspension moving in a substantially constant volume flow; and wherein the suspension is passed through a substantially vertical vessel maintained as substantially constant superatmospheric pressure and at a temperature above 80° C.; and comprising the further step of passing the suspension into and through the vessel under the influence of the pressure from a preceding continuous digestor.

12. A method as recited in claim 8 wherein steps (b) through (f) are practiced at a temperature of about 95° to 120° C.

13. A method as recited in claims 2 or 6 wherein step (b) is practiced by utilizing a device utilizing radioactivity.

14. A method as recited in claim 6 wherein steps (a) through (f) are practiced continuously with the suspension moving in a substantially constant volume flow, and with the treatment gas being added and mixed into the suspension in a substantially even flow.

15. A method as recited in claim 14 wherein the suspension is passed through a substantially vertical treatment vessel maintained at substantially constant superatmospheric pressure and at a temperature above 80° C.; and wherein step (b) is practiced by measuring the static pressure difference between two or more levels in the vertical treatment vessel.

* * * * *